United States Patent [19]

Suzuki

[11] 4,286,163
[45] Aug. 25, 1981

[54] DENTAL RADIOGRAPHIC APPARATUS FOR PHOTOGRAPHING ENTIRE JAWS

[75] Inventor: Masakazu Suzuki, Kyoto, Japan

[73] Assignee: Kabushiki Kaisha Morita Seisakusho, Kyoto, Japan

[21] Appl. No.: 131,709

[22] Filed: Mar. 19, 1980

[51] Int. Cl.³ .............................................. A61B 6/14
[52] U.S. Cl. ................................................. 250/439 P
[58] Field of Search ................................... 250/439 P

[56] References Cited

U.S. PATENT DOCUMENTS 4,039,837  8/1977  Ohta et al. ......................... 250/439 P 4,247,779  1/1981  Ciavattoni et al. ............. 250/439 P Primary Examiner—Alfred E. Smith
Assistant Examiner—T. N. Grigsby
Attorney, Agent, or Firm—Koda and Androlia

[57] ABSTRACT

The disclosure relates to a dental radiographic apparatus for photographing the entire jaws wherein the apparatus includes an X-ray generator and an X-ray film cassette holder mounted respectively at one end of a rotary arm and at the other end thereof. The apparatus electrically controls an X-ray film feed speed so as to be corresponding to and synchronous with the rotatingly travelling speed of the X-ray generator.

11 Claims, 3 Drawing Figures

DENTAL RADIOGRAPHIC APPARATUS FOR PHOTOGRAPHING ENTIRE JAWS

BACKGROUND OF THE INVENTION

1. Field of the Invention

This invention relates generally to a dental radiographic apparatus for photographing the entire jaws, and more particularly to a dental radiographic apparatus directed to changing the X-ray film feeding speed in synchronism with the speed of the X-ray generator.

2. Prior Art

Heretofore a horizontal rotary arm and an X-ray film feed mechanism were mechanically connected to each other when the speed of X-ray film feed was brought into synchronism with the rotatingly travelling speed of the X-ray generator. The mechanical connection of the kind described made the radiographic apparatus complicated in mechanism and rendered it impossible to provided correct synchronous control because of slip of the cam used in the mechanical connection.

SUMMARY OF THE INVENTION

Accordingly, in view of the disadvantages described above, it is the primary object of this invention to provide a dental radiographic apparatus for photographing the entire jaw which is directed to changing the speed of X-ray film feed in synchronism with the rotatingly travelling speed of the X-ray generator.

In keeping with the principles of this invention, the objects are achieved by the unique structure, wherein while an X-ray film cassette holder are being moved around an object in a timed relation with each other in the state of the X-ray generator and the X--ray film cassette holder being located in a mutually opposed relation with the object interposed between the generator and the holder, an X-ray beam is irradiated on the object and the X-ray beam transmitting through the object is received by the X-ray film to make a tomogram of a required curved plane so as to obtain a panoramic X-ray photograph of the entire jaws, and more particularly to a dental radiographic apparatus for photographing the entire jaws, wherein the apparatus is provided with an X-ray generator and X-ray film cassette holder and is designed to electrically control the number of rotations of the latter motor synchronously in proportion to the number of rotations of the former motor.

The object and advantages of the invention will become more apparent from a description of the invention taken in conjunction with the accompanying drawings illustrative of a preferred embodiment of the invention.

DETAILED DESCRIPTION OF THE INVENTION

Figure 1:
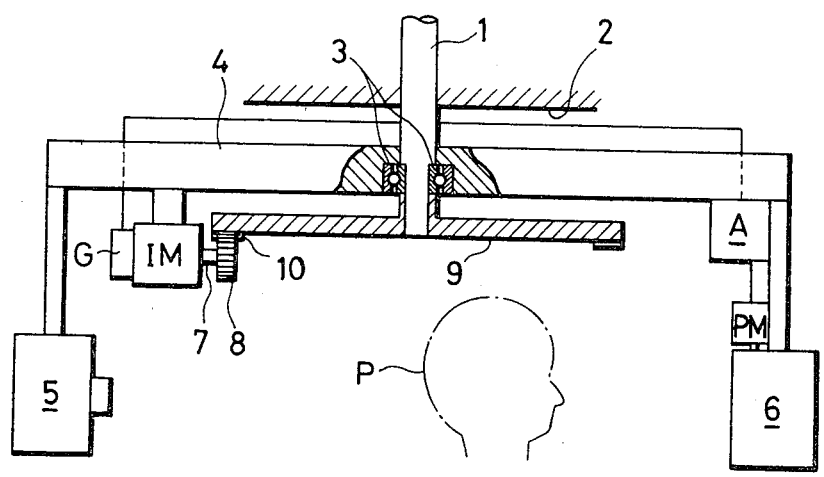
FIG. 1 is a schematic view of the mechanical component parts of the apparatus.

In FIG. 1, the numeral 1 indicates a base shaft suspended from a support base 2, and a horizontal rotary arm (to be referred to as a rotary arm) 4 is horizontally rotatably suspended by the base shaft 1 through a bearing 3. The rotary arm is provided with an X-ray generator 5 and an X-ray film cassette holder 6 which are respectively held at one end of the rotary arm 4 and at the other end thereof in an opposed relation with each other at an angular phase difference of 180°. The arm is so constructed that when X-ray photograph is taken, the arm is rotatingly moved within the same area of plane as that within which the X-ray generator 5 and X-ray film cassette holder 6 having an object P disposed therebetween encircle the object P and an X-ray rilm (not shown) is fed within the X-ray film cassette holder 6 in synchronism with the travelling speed of the arm. In order to rotate the arm 4, an induction motor IM is integrally mounted on the arm, and a pinion 3 is fixedly mounted on an output shaft 7 of the motor IM. On the other hand, a receiving plate 9 is fixedly mounted on the base shaft 1 and a rack 10 is provided circumferentially of the circle described around the base shaft 1 on the underside of this receiving plate 9 and the rack 10 is in mesh with the pinion 8. When the pinion 8 is rotated on the rack 10 in meshing with each other by the rotation of the induction motor IM, forced rotating force of the rotary arm 4 is induced by the rotation of the pinion 8 with respect to the rack 10. Also, the arm 4 is provided with a pulse motor PM for feeding the X-ray film. Both motors IM and PM are electrically connected to each other by means G for converting the number of rotations of the motor IM into an electrical signal as well as by means of a rectifier circuit 14, DC voltage-pulse converter circuits 12 and a film feed motor driving circuit 13 as particularly shown in the circuitry in FIG. 2, and the motor PM is synchronously changed in speed in proportion to the speed of rotation of the motor IM, namely the rotatingly travelling speed of rotary arm 4 and of the X-ray generator 5, thereby controlling the feed speed of X-ray film.

Figure 2:
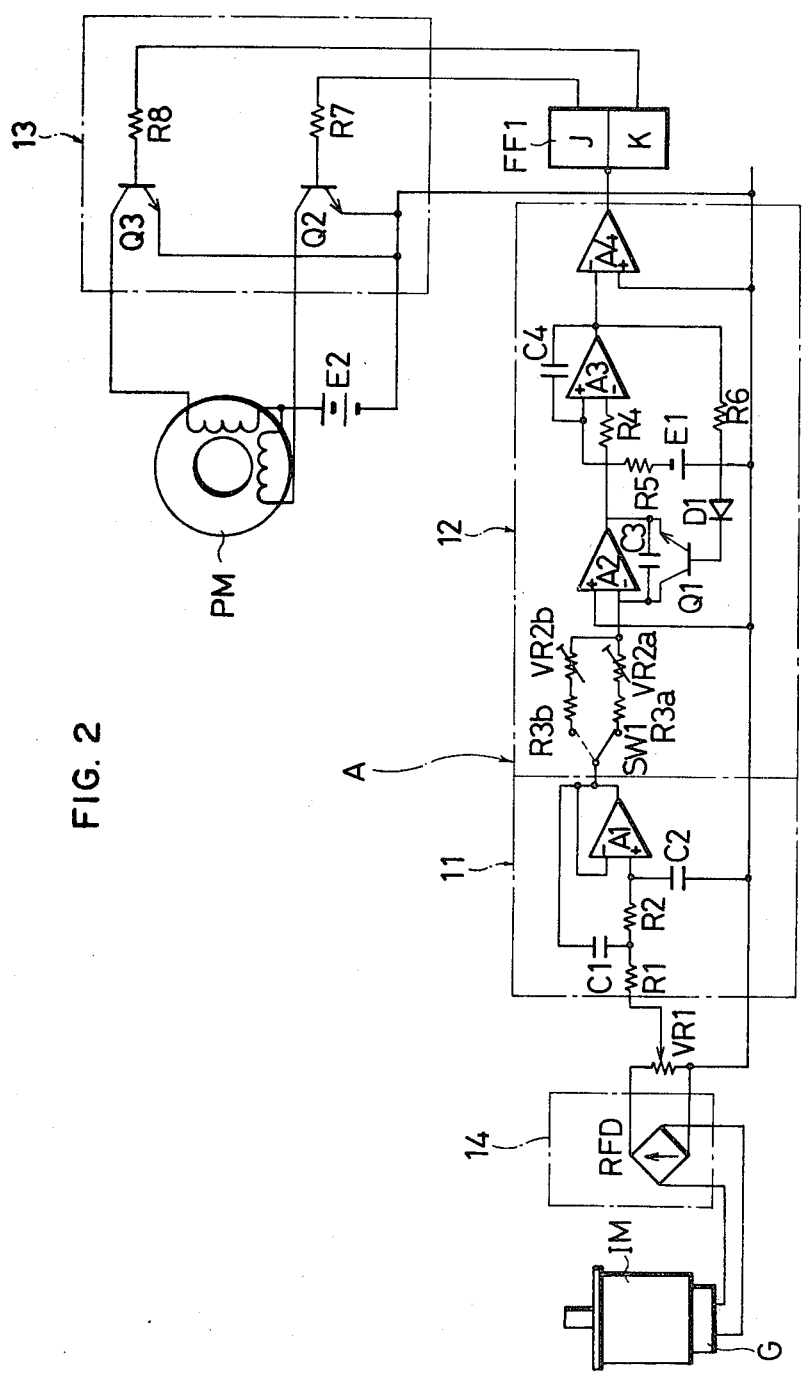
FIG. 2 is an electric circuit diagram of the apparatus.

In FIG. 2, the means for converting the number of rotations of the arm drive motor IM into an electrical signal is a tachogenerator connected directly to the output shaft 7 of the motor IM, the tachogenerator inducing AD voltage in proportion to the number of rotations of the motor IM. The character RFD designates a rectifier for converting the ÅD voltage into a pulse. The character VR1 designates a variable resistor for changing and setting a ratio of X-ray film feed speed (namely, transfer constant of a film feed motor drive control circuit A) to the number or rotations (speed of rotation) of the motor IM, namely rotatingly travelling speed of the X-ray generator 5, and the value of this variable resistor VR1 is set at a desired dose before X-ray photographing is started. The circuit including condensers C1 and C2, resistors R1 and R2, and an amplifier A1 composes a low-pass filter circuit 11 and is intended to shut off high-frequency component contained in the above pulse. Also, the numeral 12 designates DC voltage-pulse conversion circuit which includes a Miller intergration circuit, comparator circuit and buffer amplifier A4 and which produces a pulse voltage in a repetitive period proportional to an input voltage from a low-pass filter circuit 11 and functions to operate flip-flop FF1 as a trigger pulse. Transistors Q2 and Q3 compose a motor drive circuit 13 for pulse motor PM, the resistors R7 and R8 designating base resistors for the transistors Q2 and Q3. Also, a resistance series connector of resistor R3a and variable resistor VR2a and a resistance series connector of resistor R3b and variable resistor VR2b are selected by switch SW1 in the circuit 12. This selection is intended to select a conversion factor of the circuit 12, and stated more concretely, the time constant of the Miller integration circuit constructed to include amplifier A2 is determined by CR circuit between this selected resistance series connector and condenser C3. The selection of this resistance series connector is effected before starting of X-ray photographing in the same manner as setting resistance value of the variable resistor VR1. This comparator circuit compares a reference voltage source E1 with this integration output by a comparator A3, and includes resistors R4 and R5 and condenser C4.

Figure 3:
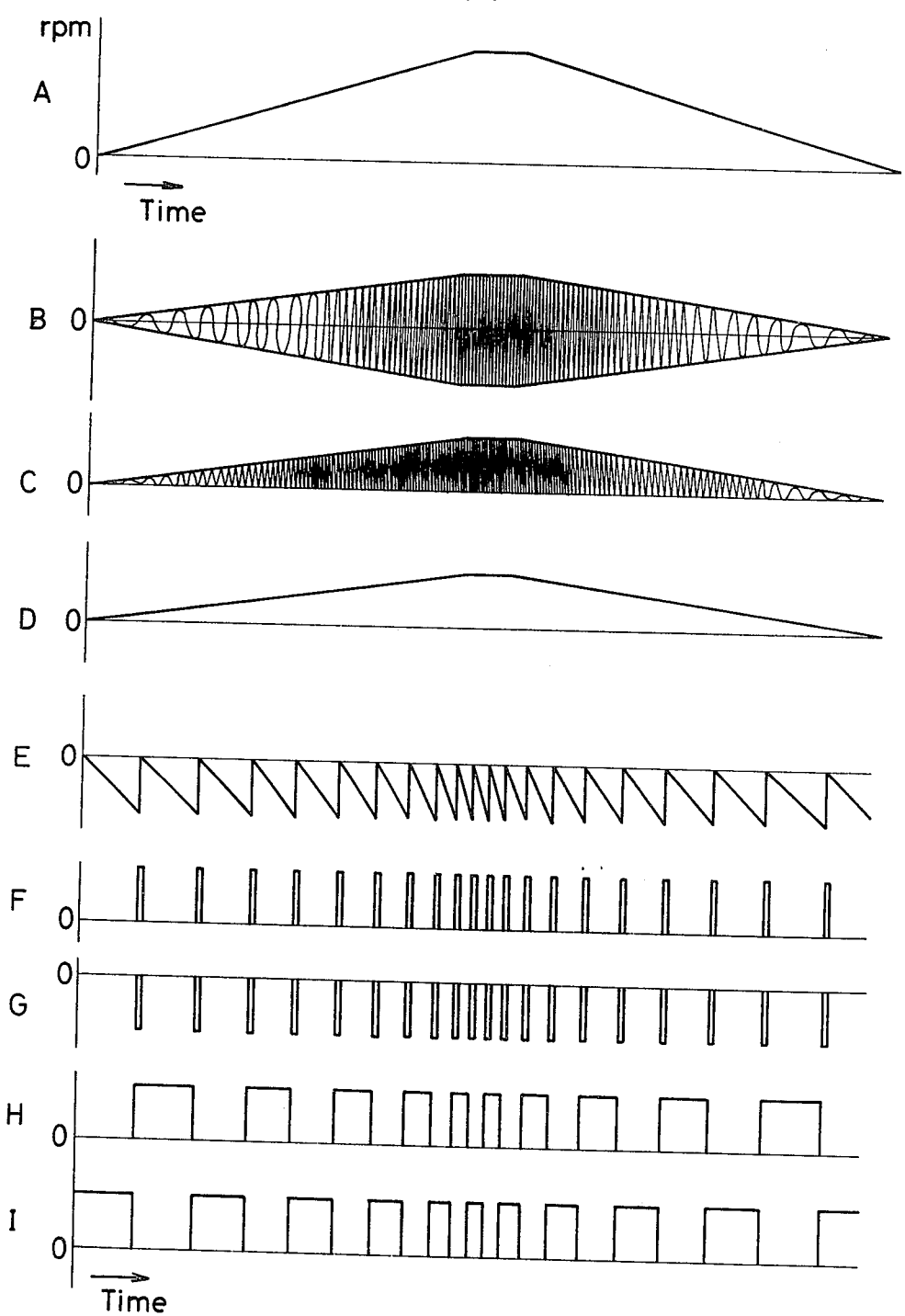
FIG. 3 is a waveform of signal of each part of the circuit for explanation of the operation.

Referring now to the operation of the circuit shown in FIG. 2 in conjunction with the signal waveform diagram in FIG. 3, the motor IM is actuated and rotatably controlled by a drive circuit (now shown) and by X-ray photographing operation. In FIG. 3A showing this output of rotation, a change in the number of rotations takes place in a substantially truncated shape as shown from the time of actuation to the time of stopping. This change is to demonstrate by the operation of the subsequent circuits the fact that the number of rotations of motor PM follow this change in the number or rotations of motor and is favorably synchronously controlled and does not mean that a change in the number of rotations of motor IM is limited to the change in FIG. 3. The number of rotations of the motor IM derived by the tachogenerator G in the form of AC voltage proportional to the number of rotations of the motor IM as shown in FIG. 3B, and the AC voltage thus obtained is changed through rectifier circuit 14 into pulse (In FIG. 3C) and has its high-frequency AC component damped by being passed from a variable resistor VR1 through low-pass filter circuit 11 and is turned into DC voltage proportional to the number of rotations of motor shown in FIG. 3D. At this time, pulse voltage passing from rectifier circuit 14 into the low-pass filter circuit 11 is given voltage change by the resistance value set by variable resistor VR1 when the pulse voltage passes through the variable resistor VR1, and accordingly, DC voltage occurring as output of the low-pass filter circuit 11 is increased or decreased in accordance with the resistance value (which is preset) of the variable resistor VR1. The output of the low-pass filter circuit 11 is supplied to an amplifier A2 through a resistor R3a and variable resistor VR2a or resistor R3b and variable resistor VR2b selected by switch SW1 and is integrated, and generates a saw tooth wave (FIG. 3E) of frequency proportional to the above output voltage. Simultaneously, comparison is made by a comparator A3 between Miller integration circuit output voltage and reference voltage source (E1), and when integration output exceeds reference voltage, the comparator A2 outputs positive output voltage, and this voltage is fed back to Mill integration circuit through resistor R6 and diode D1, and transistor Q1 is biased and energized and discharges a condenser C3. But Miller integration is instantly reduced to zero. The output voltage of comparator A2 is held at the same voltage for a certain time t as shown in FIG. 3F by the time constant determined by condenser C4 and resistor R5 and subsequently thereto, the output is stopped to deenergize transistor Q1, with the result that integration operation is again started. A positive pulse synchronous with the saw tooth wave as shown in FIG. 3F is outputted by this repeated operation from the comparator A3 and this positive pulse is led to the buffer amplifier A4 where the positive pulse is reversed to a negative pulse and flip-flop FF1, the pulse output shown in FIGS. 3H and 3E is alternately produced each time the flip-flop FF1 is triggered by the output of the buffer amplifier (FIG. 3G) to thereby energize transistors Q2 and Q3 of motor drive circuit 13 alternately and to drive the pulse motor PM by the drive source E2 of the motor PM to turn the motor PM and feed the X-ray film. At this time, the pulse intervals of output of the buffer amplifier are in a synchronized relation with respect to the saw tooth wave (FIG. 3E) and accordingly, the pulse intervals are proportional to the number of rotations of the motor IM, and in consequence, the output intervals of the flip-flop FF1 triggered by the output of the buffer amplifier are also brought into proportion to the number of rotations of the motor IM, so that the motor PM is synchronized with the motor IM to thereby change the speed of rotations.

As apparent from the description given above, this invention is so designed that a motor for feeding an X-ray film is provided independent of a motor for rotatingly driving a horizontal rotary arm, the number of rotations of the former motor, namely, the horizontally travelling speed of the horizontal rotary arm and of X-ray generator is converted into an electrical signal and is derived as the signal and the number of rotations of the latter motor is controlled in proportion to the increase or decrease of the electrical signal. Accordingly, the feed of X-ray film is effected in a precisely synchronized relation with an X-ray exposure dose to provide a clear and sharp tomogram. Particularly, it was a general practice in the prior art to mechanically connect an X-ray film feed mechanism with the horizontally travelling arm so as to bring the speed of X-ray film feed in synchronism with the rotatingly travelling speed of X-ray generator, and in consequence the radiographic apparatus was invariably complicated in mechanism, which, in turn, made it impossible to provide precise synchronous control because of slip of the cam used in the mechanical connection. This invention obviates the drawbacks of the kind described above.

It is to be understood that the invention is not limited in its application of details of construction and arrangement of parts illustrated in the accompanying drawings, since the invention is capable of other embodiments of being practiced or carried out in various ways. Also, it is to be understood that the phraseology or terminology employed herein is for the purpose of description and not of limitation.

I claim:

1. A dental radiographic apparatus for photographing the entire jaws wherein the apparatus includes a horizontal rotary arm and a drive motor for rotating said horizontal rotary arm, said arm having an X-ray generator at one end thereof and having an X-ray film cassette holder for a film cassette containing an X-ray film therein at the other end thereof in such manner as to dispose an object between the generator and the cassette holder and said arm further being designed to make a tomogram of the entire jaws of said object by driving said rotary arm drive motor, said photographic apparatus being characterized in that the apparatus includes a film feed motor different from said rotary arm drive motor and adapted to feed the film in said film cassette holder, a means for converting the number of rotations of said rotary arm drive motor into an electrical signal and a film feed motor drive control circuit for variably controlling the number or rotations of said film feed motor by following and in synchronism with the number of rotations of said rotary arm drive motor.

2. An apparatus according to claim 1, wherein said film feed motor drive control circuit comprises a rectifier circuit, a DC voltage-pulse converter circuit, and a drive circuit for said film feed motor.

3. An apparatus according to claim 1 wherein said means for converting the number of rotations of said rotary arm drive motor into an electrical signal converts the number of rotations of the rotary arm drive motor into an electromotive force proportional to the number of rotations of the rotary arm drive motor.

4. An apparatus according to claim 2, wherein said rotary arm drive motor is an induction motor.

5. An apparatus according to claim 1, wherein said film feed motor is a pulse-driven motor.

6. An apparatus according to claim 2, wherein said film feed drive control circuit outputs a pulse signal having a repetitive period variable in response to an AC electromotive force generated in response to the number of rotations of said rotary arm drive motor and drives the film feed motor by means of a pulse.

7. An apparatus according to claim 2, wherein a means for converting the number of rotations of said rotary arm drive motor into an electromotive force is a tachogenerator connected to the rotary arm drive motor.

8. An apparatus according to claims 3 or 4, wherein said pulse-driven motor is a two-phase pulse motor.

9. An apparatus according to claim 1, wherein said film feed motor drive control circuit is enabled to vary a transfer constant of the circuit.

10. An apparatus according to claim 9, wherein a means for varying the transfer constant of said film feed motor drive control circuit is enabled to vary said AC electromotive force by use of variable resistor.

11. An apparatus according to claim 1, wherein said film feed motor is a pulse-driven motor, said means for converting the number of rotations of said rotary arm drive motor into an electrical signal as a tachogenerator connected to the rotary arm drive motor, and said film motor drive control circuit follows and varies a repetitive period of output pulse in response to the output of said tachogenerator.

\* \* \* \* \*